United States Patent [19]

Costa

[11] 4,317,946

[45] Mar. 2, 1982

[54] PROCESS FOR PRODUCING ETHYLENE GLYCOL VIA CATALYTIC HYDROGENATION OF GLYCOLALDEHYDE

[75] Inventor: Lawrence C. Costa, Nanuet, N.Y.

[73] Assignee: The Halcon SD Group, Inc., New York, N.Y.

[21] Appl. No.: 163,550

[22] Filed: Jun. 27, 1980

[51] Int. Cl.$^3$ .............................................. C07C 31/20
[52] U.S. Cl. .................................................... 568/862
[58] Field of Search ......................................... 568/862

[56] References Cited

U.S. PATENT DOCUMENTS

| | | |
|---|---|---|
| 2,451,333 | 10/1948 | Gresham et al. . |
| 3,454,644 | 7/1969 | Dewhirst . |
| 3,857,900 | 12/1974 | Wilkinson . |
| 3,935,284 | 1/1976 | Kruse . |
| 4,024,193 | 5/1977 | Kruse . |
| 4,079,085 | 3/1978 | Wall . |
| 4,144,401 | 3/1979 | Wall . |
| 4,170,605 | 10/1979 | Williamson et al. . |
| 4,170,606 | 10/1979 | Williamson et al. . |

FOREIGN PATENT DOCUMENTS

| | | |
|---|---|---|
| 2908 | 7/1979 | European Pat. Off. . |
| 2741589 | 3/1978 | Fed. Rep. of Germany . |
| 2016006 | 9/1979 | United Kingdom . |
| 2024811 | 1/1980 | United Kingdom . |

OTHER PUBLICATIONS

*Abstracts of the 179th Meeting of the American Chemical Society,* Petr. No. 28, Grey et al., "Novel Anionic Phosphine Transition Metal Hydride Complexes and their Application to the Catalytic Hydrogenation of Polor Organic Compounds".
*Chemical Abstracts,* vol. 87, 1977, No. 135822m, Cole-Hamilton, D. J. et al.
*Chemical Abstracts,* vol. 83, 1975, No. 163562n, Imai H. et al.
*Chemical Abstracts,* vol. 91, 1979, No. 192782e, Ito, T. et al.
*Chemical Abstracts,* vol. 88, 1978, No. 89065n, Horino, H. et al.
*Chemical Abstracts,* vol. 79, 1973, No. 140043x, Frediani, P. et al.
*Chemical Abstracts,* vol. 86, 1977, No. 170448v, Tasumi, T. et al.
Strohmeimer, W. et al., *J. Organomet. Chem.,* vol. 171, 1979, pp. 121–129.
Skapski, A. C. et al., *J. Chem. Soc.,* (Dalton), 1974, pp. 390–395.
Dobson, A. et al., *Inorg. Chem.* vol. 16, 1977, pp. 137–142.
Legzdins, P. et al., *J. Chem. Soc.,* (A), 1970, pp. 3322–3326.
Strohmeimer, W. et al., *J. Organomet. Chem.,* vol. 145, 1978, pp. 189–194.
Mitchell, R. W. et al., *J. Chem. Soc.,* (Dalton), 1973, pp. 846–854.
Sanchez-Delgado, R. A., *J. Mol. Cat.,* 1979, pp. 303–305.
Joo, F. et al., *Inorg. Chimica Acta.,* vol. 25 1977, L61–62.
Gargano, M. et al., *J. Organomet. Chem.,* vol. 129, 1977, pp. 239–242.
Schruck, R. R. et al., *Chem. Comm.,* 1970, pp. 567–568.
Frediani, P. et al., *J. Organomet. Chem.,* vol. 150, 1978, pp. 273–278.
Rose, D. et al., *J. Chem. Soc.* (A), 1969, pp. 2610–2615.

*Primary Examiner*—Nicky Chan
*Assistant Examiner*—Frederick W. Pepper
*Attorney, Agent, or Firm*—William C. Long; David Dick; Riggs. T. Steward

[57] ABSTRACT

A process is provided for catalytic hydrogenation of glycolaldehyde to form ethylene glycol in liquid phase employing a homogeneous ruthenium carboxylate complex catalyst system. Ethylene glycol is produced in excellent yields and selectivities and the process permits use of mild temperature and pressure conditions. The formation of acetals is greatly minimized as compared to prior art ruthenium catalysts.

12 Claims, No Drawings

PROCESS FOR PRODUCING ETHYLENE GLYCOL VIA CATALYTIC HYDROGENATION OF GLYCOLALDEHYDE

BACKGROUND OF THE INVENTION

1. Field of the Invention

This invention relates to the production of ethylene glycol, and more specifically to the hydrogenation of glycolaldehyde in homogeneous catalysis systems.

2. Description of the Prior Art

Ethylene glycol is a chemical of acknowledged commercial importance, which is used widely in the preparation of anti-freeze compositions and in the manufacture of fiber, as well as in other uses. Ethylene glycol manufacturing processes of commercial interest have generally been based on ethylene oxide as a raw material. Other processes have been developed which make it possible to produce ethylene glycol, without the necessity for the intermediate manufacture of the epoxide, by a liquid phase reaction of olefin, carboxylic acid and molecular oxygen in the presence of a catalyst to produce carboxylic acid esters of the glycol. The glycol can then be liberated by hydrolysis of the esters.

Ethylene glycol has also been prepared by catalytic reaction of carbon monoxide and hydrogen. Thus, for example, U.S. Pat. No. 4,170,605 relates to a process for reacting carbon monoxide and hydrogen with certain ruthenium catalysts and a pyridine base ligand. However, high pressures are required for the reaction. Other processes include those disclosed in U.S. Pat. No. 4,170,606 (using an iridium complex catalyst) and published British Patent Application No. 2016006A (employing rhodium carbonyl phosphido cluster compounds).

Ethylene glycol has also been formed, albeit not commercially, by hydroformylation processes, wherein hydrogen and carbon monoxide are reacted with formaldehyde in the presence of certain catalyst systems. Exemplary of such processes are those disclosed in U.S. Pat. Nos. 4,079,085 (catalyst comprising cobalt carbonyl and rhodium) and 4,144,401 (catalyst comprising a rhodium compound), and 2,451,333 (catalyst compounds of Ni, Co, Mn, Fe, Cr, Cu, Pt, Mo, Pd, Zn, Cd, Ru, and especially Co). All of the hydroformylation processes, however, suffer from a relatively low yield of ethylene glycol and a poor selectivity to the desired product.

To avoid these disadvantages, European Patent Application 2,908 (1979) and German Pat. No. 2,741,589 (1978) sought to hydrogenate glycolaldehyde in the presence of certain hydrogenation catalysts to form ethylene glycol. The glycolaldehyde is formed from the hydroformylation of formaldehyde employing certain rhodium catalysts. European Patent Application No. 2,908 discloses hydrogenation of glycolaldehyde in aqueous solution employing Raney nickel, palladium or platinum heterogeneous catalysts. German Pat. No. 2,741,589 also envisions use of rhodium catalysts in hydrogenation of glycolaldehyde to form ethylene glycol, although the patent discloses that increased ethylene glycol yields can be obtained by use of palladium and nickel metal catalysts in the hydrogenation reaction.

In hydrogenations generally, it is well known that hydrogenation processes can be broadly classified into one of two categories, depending upon the physical phase in which the catalyst is present during the hydrogenation process. In the first type, the catalyst is essentially insoluble in the reaction medium; this is referred to as a heterogeneous hydrogenation process. In contrast, a homogeneous hydrogenation process describes a process in which the catalyst is essentially completely soluble in the reaction medium. Homogeneous hydrogenations typically allow use of milder process conditions than are necessary with heterogeneous catalysis, which would be industrially desirable.

Exemplary of the prior art homogenous hydrogenation processes employing ketones as feed are U.S. Pat. Nos. 3,935,284 (ruthenium triphenylphosphine complex plus a strong acid; hydrogenation of certain saccharides), and 4,024,193 (ruthenium triphenylphosphine complex and a strong acid; hydrogenation of described ketones, e.g., hydrogenation of 1,3-dihydroxy acetone to glycerol). Literature references to homogenous hydrogenations of ketones to alcohols include R. R. Schrock, et al., Chem. Comm., pages 567–568 (1970); W. Strohmeier, et al., J. Organomet. Chem., Vol. 171, pages 121–129 (1979); P. Frediani, et al., J. Organomet. Chem., Vol. 150, pages 273–278 (1978); T. Tasumi, et al., 86 Chem. Abs., 170,448v (1977); and M. Gargano, et al., J. Organomet. Chem., Vol. 129, pages 239–242 (1977).

Various catalysts for the homogeneous hydrogenation of aldehydes have been proposed, such as various ruthenium compounds and complexes, in particular complexes of ruthenium containing triorganophosphine ligands and one or more of hydrido, halide, carbonyl, cyanate, thiocyanate and cyanide groups associated with the complex. Illustrative ruthenium complexes disclosed by the prior art for aldehyde hydrogenations, therefore, are those disclosed in U.S. Pat. No. 3,454,644 (complexes of the formula $L_nRuX_2$ wherein L is a triphenylphosphine ligand, n is an integer of 3 to 4 and X is a halogen or hydrogen); U.S. Pat. No. 3,857,900 (complexes of the formula $L_nRuX_y$ wherein L is again triphenylphosphine, n and y are each integers associated with the valence state of the ruthenium atom and X is halogen or "pseudohalogen", namely, cyanide, cyanate or thiocyanate); R. A. Sanchez-Delgado, et al., J. Mol. Cat., Vol. 6, pages 303–305 (1979) (RuHCl(CO)(P$\phi$3)3, RuHCl(P$\phi$3)3; RuCl2(P$\phi$3)3, Ru(CO)3(P$\phi$3)2); W. Strohmeier, et al., J. Organomet. Chem., Vol. 145, pages 189–194 (1978) (catalyst comprising Cl2(CO)2Ru(P$\phi$3)2).

See also, 79 Chem. Abs., 140,043 (1973), reporting studies of [Ru(CO)2P$\phi$3X2]2, in which X is Cl, Br or I and Co2(CO)8, as aldehyde hydrogenation catalysts.

Other ruthenium complexes have been developed and have been found useful catalysts in the hydrogenation of various alkenes and alkynes. Among these the ruthenium triphenylphosphine complexes also containing carboxylate groups, alone or in combination with hydrido groups, have been found to be useful catalysts with these alkenes and alkynes. However, it is not possible from this work with ruthenium carboxylate triphenylphosphine complexes, which involved the hydrogenation of carbon-carbon unsaturation, to conclude anything with respect to the utility of similar or the same carboxylate complexes in the hydrogenation of aldehydes. Indeed, in a study of the reverse reaction, viz. the dehydrogenation of primary alcohols to yield aldehydes, it was found by A. Dobson, et al., 16 Inorg. Chem., 137 (1977) that perfluorosubstituted $R_F$ groups are essential in complexes of the formula Ru(O2CR$_F$)2-

(CO)(Pφ₃)₂, wherein $R_F$ is —CF₃, —C₂F₅ or —C₆F₅, in order for the observed catalytic dehydrogenation to occur, and that other ruthenium carboxylate complexes, such as bis(acetato)bis(triphenylphosphine)ruthenium carbonyl, which do not contain such essential $R_F$ ligands are not effective catalysts for such a dehydrogenation reaction.

The complexity of homogeneous hydrogenation systems is underscored by the observed catalysis of aldehyde self-esterifications, which has been reported for a hydrido ruthenium phosphine catalyst, dihydridotetrakis(triphenylphosphine)ruthenium. For example, this complex is known to catalyze the self-esterification of acetaldehyde to form large amounts of $CH_3CO_2CH_2CH_3$. T. Ito, et al., 91 Chem. Abs., 192,782e (1979). See also, H. Horino, et al., 88 Chem. Abs., 89,065n (1978), and D. J. Cole-Hamilton, 87 i Chem. Abs., 135,822m (1977).

$RuH_2(P\phi_3)_4$ is known to catalyze H transfer reactions between n-$C_5H_{11}CHO$ and various solvents (such as certain ethers, hydroaromatic compounds, and alcohols) further increasing the number of potential by-products employing these Ru catalysts in the presence of such solvents. H. Imai, et al., 83 Chem. Abs., 163,562n (1975).

The aforementioned art dealing with ruthenium-catalyzed hydrogenations of alkenes and alkynes can be supplemented by the following references: P. L. Legzdins, et al., J. Chem. Soc. (A), 3322(1970)(Ru₂(O₂CCH₃)₄, 2Pφ₃ and Ru₂(O₂CCH₃)₄Cl); R. W. Mitchell, et al., J. Chem. Soc. (Dalton) 846 (1973) (RuH(O₂CCH₃)(Pφ₃)₃, Ru(H)₂(Pφ₃)₄, and Ru(O₂CCH₃)₂(Pφ₃)₂); D. Rose, et al., J. Chem. Soc. (A) 2610 (1969) (RuH(O₂CR)(Pφ₃)₃, in which R is —CF₃, —CH₃, —CH₂Cl, —C₂H₅, —CH₂CH₂CH₃, —CH(CH₃)₂, —C(CH₃)₃, —φ or —φOH); A. C. Skapski, et al., J. Chem. Soc. Dalton 390 (1974) (hydridoacetatotris(triphenylsphosphine)ruthenium). However, the activity of the foregoing ruthenium-carboxylate complexes for hydrogenation of such alkenes and alkynes was not found to follow a predictable path by these researchers. For example, P. L. Legzdins, et al., in the J. Chem. Soc. (A), 3322 (1970) reference found diruthenium tetraacetatodi(triphenylphosphine) to catalyze the rapid hydrogenation of cyclo-octa-1,5-diene, but no hydrogenation of the structurally similar cyclo-octa-1,3-diene was observed with this catalyst. Also, this ruthenium complex was not found to catalyze the hydrogenation of the hydroxy-substituted alkyne, propargyl alcohol (HOCH₂C≡CH).

D. Rose, et al., in their J. Chem. Soc. (A) 2610 (1969) paper noted that the failure of hydridoacetatotris(triphenylphosphine)ruthenium to catalyze the hydrogenation of allyl alcohol (HOCH₂CH=CH₂) sharply contrasted with the rapid hydrogenation of this alcohol using known rhodium complexes, RhCl(Pφ₃)₃ and RhH(CO)(Pφ₃)₃.

Ruthenium complexes containing sulfonated triphenylphosphine ligands have been reported to be catalysts in aqueous solutions for the homogeneous hydrogenation of oxo and olefinic groups in certain carboxylic acids. F. Joo, et al., 25 Inorg. Chimica. Acta. L61–L62 (1977). The complexes studied were HRu(O₂CCH₃)(Dpm)₃; RuCl₂(Dpm)₂; and HRuCl(Dpm)₃, in which "Dpm" is a sulfonated triphenylphosphine group.

SUMMARY OF THE INVENTION

According to the process of this invention, glycolaldehyde is hydrogenated to form ethylene glycol in high yields and in excellent selectivities by reacting glycolaldehyde in liquid medium with hydrogen in the presence of an effective amount of a catalyst comprising a complex of the formula:

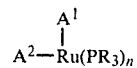

wherein n is 2 or 3, $A^1$ is hydrogen or a carboxylic moiety derived from an aromatic or saturated aliphatic monocarboxylic acid, $A^2$ is a carboxylate moiety derived from an aromatic or saturated aliphatic monocarboxylic acid, and R is aryl, with the proviso that n=3 when $A^1$ is hydrogen.

It has been surprisingly found that the catalysts of this invention can effect high conversions of glycolaldehyde to ethylene glycol while significantly limiting the formation of acetals which result when other ruthenium complexes, such as RuCl₂(Pφ₃)₃, HRuCl(Pφ₃)₃, RuCl₂(CO)₂(Pφ₃)₂ and the like, are employed. These acetals, which are formed by reaction of the glycolaldehyde with the product ethylene glycol, with hydroxylic solvents and with itself, are highly undesirable since they are not readily converted to ethylene glycol on recycle to the hydrogenation, but require further processing.

The discovery that the foregoing class of ruthenium carboxylate triaryl-phosphine complexes are highly active and selective homogeneous hydrogenation catalysts for glycolaldehyde is particularly surprising in view of the teaching of the prior art that non-perfluorinated carboxylate complexes of ruthenium do not catalyze the dehydrogenation of alcohols, and are inactive in the hydrogenation of the hydroxy-substituted alkene and alkyne: HOCH₂CH=CH₂ and HOCH₂≡CH, which are structurally very similar to glycolaldehyde.

DETAILED DESCRIPTION OF THE INVENTION

The ruthenium carboxylate triaryl-phosphine catalysts (also herein termed "ruthenium carboxylate catalysts") charged to the process of this invention comprise complexes of the formula (I):

(I)

wherein n is 2 or 3, $A^1$ is hydrogen or a carboxylate moiety derived from an aromatic or saturated aliphatic monocarboxylic acid, $A^2$ is a carboxylate moiety derived from an aromatic or saturated aliphatic monocarboxylic acid, and R is aryl, with the proviso that n=3 when $A^1$ is hydrogen.

Carboxylic acids from which the foregoing $A^1$ and $A^2$ carboxylate groups can be derived include aliphatic saturated monocarboxylic acids having from 1 to 20 carbon atoms, preferably from 1 to 10 carbon atoms, and more preferably from 1 to 4 carbon atoms. Aromatic monocarboxylic acids from which the foregoing $A^1$ and $A^2$ carboxylate groups can be derived include mono- and poly-nuclear aromatic acids having from 7 to 14 carbon atoms. The foregoing saturated aliphatic carboxylic acids can be either straight-chained or branched-chained, and the aliphatic and aromatic carboxylic acids can be substituted or unsubstituted. When substituted, suitable substituents include halo (Cl, Br, I, F), alkyl of 1 to 10 carbon atoms (e.g., methyl, ethyl, hexyl, decyl and the like), alkoxy of 1 to 8 carbon atoms (e.g., methoxy, ethoxy, propoxy and the like), acyl of 1 to 10 carbon atoms (e.g., acetyl, valeroyl, benzoyl and the like), cyano, tertiary amido of from 2 to 14 carbon atoms (e.g., N,N-dimethyl-carbamido, N,N-di-n-butyl-carbamido, N,N-diphenyl-carbamido and the like), carboxyalkyl of from 2 to 10 carbon atoms (e.g., carboxymethyl, carboxybutyl, carboxyheptyl and the like), hydroxy and cycloalkyl of from 3 to 8 carbon atoms (e.g., cyclopropyl, cyclohexyl, cyclooctyl and the like). Preferred are carboxylates whose corresponding acids possess dissociation constants ($pK_a$) in aqueous solutions at 25° C. of at least 2.5. Exemplary of suitable $A^1$ and $A^2$ carboxylate moieties are formate, acetate, n-buryrate, isobutyrate, prioionate, heptanoate, decanoate, dodecanoate, 2-ethyl-hexanoate, benzoate, toluate, naphthalate, 2-hydroxy-4-chloro-pentanoate, 2,4-dihydroxybenzoate, 3-cyclopropyl-n-butyrate, and the like.

The "R" groups comprise mono- or poly-nuclear aryl having from 7 to 14 carbon atoms, such as phenyl, naphthyl and the like and can be substituted or unsubstituted. Suitable substituents include any of the halo, alkyl, alkoxy, acyl, cyano, tertiary amido, carboxyalkyl, hydroxy and cyclo-alkyl groups discussed above as suitable substituents in the $A^1$ and $A^2$ carboxylate groups. Exemplary of such substituted "R" groups are tolyl, 2-ethyl phenyl, 3-methoxy phenyl, 2,4-dichloro phenyl, 3-carboxy methyl phenyl, 2,4-dihydroxy phenyl, para-cyclohexyl phenyl, 2-chloro-3-hydroxy-naphthyl, xylyl and the like.

Illustrative ruthenium carboxylate catalysts charged to the process of this invention are:

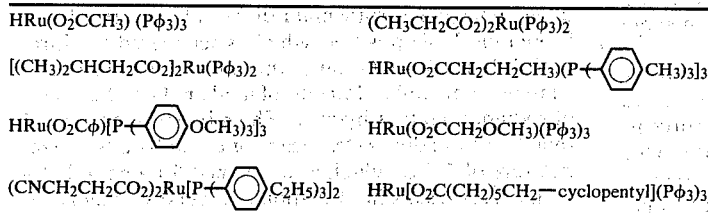

and the like.

Preferred carboxylate catalysts of this invention comprise at least one member selected from the group consisting of (a) complexes of the formula (I) above wherein $A^2$ is alkanoate of from 1 to 4 carbon atoms and $A^1$ is hydrogen, and (b) complexes of the formula (I) above wherein $A^1$ and $A^2$ are each alkanoate of from 1 to 4 carbon atoms. Still more preferred are carboxylate catalysts of formula (I) above wherein $A^1$ is H or alkanoate of 1 to 4 carbon atoms, $A^2$ is alkanoate of 1 to 4 carbon atoms and R is phenyl. Examples of the more preferred catalysts are $HRu(O_2CCH_3)(P\phi_3)_3$; $(C_2H_5CO_2)_2Ru(P\phi_3)_2$; and the like.

The foregoing ruthenium carboxylate catalysts can be prepared by known means, as for example by the methods described in D. Rose, et al., *J. Chem. Soc.* (A), 2610 (1969), and R. W. Mitchell, et al., *J. Chem. Soc.* (Dalton) 846 (1973).

In addition to the glycolaldehyde and selected ruthenium carboxylate catalyst, the liquid reaction medium will also contain a solvent for the glycol aldehyde and the selected catalyst. The solvents which are suitable for use will vary widely depending on the precise catalyst selected and will include organic solvents such as alcohols, such as the lower alkanols (e.g., methanol, ethanol, isopropyl alcohol, propanol and the like); glycols (e.g., ethylene glycol, diethylene glycol, propylene glycol); aromatic solvents (such as benzene, toluene, the xylenes and the like; aromatic and aliphatic nitriles (such as acetonitrile, propionitrile, benzonitrile, and the like); amides (such as N,N-dimethyl formamide, N,N-dimethyl acetamide, N-methyl pyrollidinone, and the like); ketones (acetone, acetophenone, methyl ethyl ketone); esters (ethyl acetate, methyl benzoate); ethers (diethyl ether, THF, diglyme, triglyme) and mixtures thereof. Preferred solvents are lower alkanols, lower alkylene glycols, ketones of 5 or fewer carbon atoms, esters of 6 or fewer carbon atoms, and ethers of at least 4 carbon atoms. Exemplary of preferred solvents are methanol, ethanol, isopropyl alcohol, propanol, butanol, pentanol, hexanol, ethylene glycol, propylene glycol, acetone, methyl ethyl ketone, ethyl acetate, diglyme and triglyme. The selected organic solvent can also contain water, preferably in amounts of less than 50 wt. % of the organic solvent.

The amount of solvent which is employed can vary widely again depending on such factors as the precise solvent and catalyst selected, temperature and other factors. Sufficient solvent should be employed to dissolve the selected ruthenium carboxylate catalyst to provide the homogeneous catalyst system of this invention.

One great advantage of the improved process of this invention is the obtention of high yields and selectivities to ethylene glycol without the need for use of severe conditions of temperature or pressure. Thus, the mild temperature and pressure conditions which are possible avoid disadvantages associated with prior art processes. Generally, the temperature of the liquid reaction medium in this invention will range from about 50° to about 200° C., and more preferably from about 75° to 180° C., and most preferably from about 100° to 150° C. While temperatures of less than 50° C. can be employed, the rates of reaction are slower and tend to become uneconomic. Similarly, while temperatures greater than 200° C. can be employed, the rate of hydrogenation is not thereby substantially increased and the decomposition of catalyst and by-product formation problems can occur to sometimes render such conditions uneconomic under some conditions.

Generally a hydrogen pressure of from about 15 to 2500 psig, and more preferably from about 100 to 2000 psig, and most preferably from 600 to 1500 psig, will be employed in the practice of this invention. It will also be understood that continuous or intermittent introduction of hydrogen to the reaction zone may be necessary to maintain the selected hydrogen pressure since hydrogen is consumed during the reaction.

The ruthenium carboxylate catalysts of this invention are employed in catalytic quantities. Amounts of the catalyst from about 0.01 wt. % to about 20 wt. % based on the glycolaldehyde charged to the hydrogenation are satisfactory, although amounts from about 0.1 wt. % to about 5.0 wt. % on the same basis are preferred. Use of less than about 0.01 wt. % catalyst concentrations will be generally uneconomic due to the decreased rates of hydrogenation which can result. Also, while greater than 20 wt. % catalyst concentrations can be used, the added cost of the catalyst can outweigh the economic benefit to be derived from any increase in the rate of hydrogenation thereby obtained.

The period of time required for the reaction to reach completion will vary widely depending on such factors as reactant concentrations, $H_2$ pressure, temperature and the like, but will generally range from about 1 to 10 hours, more usually from about 2 to 4 hours. The liquid reaction medium can be agitated if desired during the course of the reaction to maintain intimate contacting of the gaseous hydrogen with the components of the liquid reaction mixture. Means by which such agitation can be performed are conventional and need not be described.

The selected ruthenium carboxylate catalyst will be generally employed in an amount sufficient to provide at least about $1 \times 10^{-5}$ mole, and preferably at least about $1 \times 10^{-4}$ mole, of ruthenium catalyst (calculated as ruthenium) per mole of glycolaldehyde present in the liquid reaction medium. While lower amounts can also be used, rates of hydrogenation are decreased. To avoid the slow rates of hydrogenation to ethylene glycol which have been found to occur under certain conditions, a molar ratio of the selected ruthenium carboxylate catalyst to glycolaldehyde present in the liquid reaction medium of at least about 0.004:1 is preferably used when both the hydrogen pressure is less than 500 psig and the temperature is outside the range of from about 100° C. to 120° C.

The methods by which the reactants and catalysts are contacted are not critical and can vary widely. Thus, one or more of the glycolaldehyde, selected solvents and catalysts can be premixed or charged directly to the reaction zone. Similarly, the gaseous hydrogen reactant can be premixed with one or more of the liquid components of the feed or can be separately charged to the reaction zone. The methods of contacting the gaseous hydrogen with the liquid reaction medium is not critical and illustrative are the conventional methods of gas sparging employing conventional gas sparging apparatus.

The concentration of glycolaldehyde in the liquid reaction medium is not critical and will vary widely depending upon such factors as temperature, solubility of glycolaldehyde in the select solvent and other factors. Generally, the glycolaldehyde concentration will be from about 1.0 to about 20 wt. % of the total liquid reaction medium.

Subsequent to the reaction, the product mixture is separated and the desired product is recovered by conventional means such as fractional distillation, selective extraction, chromatographic techniques and the like. Unreacted glycolaldehyde can be recovered and recycled to the reaction, if desired. Similarly, the recovered ruthenium carboxylate catalysts can also be recycled to the reaction since it has been found that the activity of the catalyst is not thereby diminished.

The glycolaldehyde and selected ruthenium carboxylate catalysts of this invention are preferably contacted in the substantial absence of molecular oxygen, since it has been found that while the ruthenium carboxylate catalyst are relatively stable to oxygen when the catalysts are in solid form, they exhibit a sensitivity to molecular oxygen when the catalysts are dissolved in a liquid. By "substantial absence of molecular oxygen" herein is meant that the concentration of $O_2$ in the gas phase above the liquid reaction medium is maintained at a level of not greater than about 1.0 wt. % of oxygen. More preferably, the oxygen concentration in the gas phase is less than about 0.10 wt. %. The reaction can therefore be conducted in the presence of an inert gas for the reaction. Suitable inert gases are nitrogen, helium, argon and the like.

The process of this invention can be further illustrated by reference to the following Examples, wherein parts are by weight unless otherwise indicated. In each Example, the reaction vessel is flushed with $H_2$ to remove substantially all $O_2$ from above the liquid reaction mixture. All liquid samples are analyzed by gas chromatography. Yields, selectivities and conversions are reported based on the amount of glycolaldehyde charged to the reaction vessel. In Examples 2-5, 7-9, 11, 12, 17 and 19 the product mixture is found to contain no detectable acetal by-products, to a level of sensitivity of 0.01 wt. %.

EXAMPLE 1

Preparation of $RuH(O_2CCH_3)(P\phi_3)_3$

To a 100 cc glass flask is added 50 mls. of methanol, 5.0 gram of triphenylphosphine and 1.0 gram of ruthenium trichloride hydrate. The resulting mixture is stirred and heated by means of an oil bath under an atmosphere of nitrogen to a temperature of 75° C. and maintained at that temperature for 6 hours. Tris(triphenylphosphine) ruthenium dichloride is formed as a brown insoluble powder, which is recovered by filtration (3.9 gram). 1.0 Gram of this powder is dissolved in a mixture containing 150 mls. of methanol and 1.5 grams of sodium acetate trihydrate. The mixture is stirred and then heated under $N_2$ by means of an oil bath to a temperature of 75° C. which is maintained for a period of 4 hours. This results in formation of a yellow precipitate, which is recovered by filtration and is identified as the desired hydridoacetato tris(triphenylphosphine) ruthenium (0.8 gram).

EXAMPLE 2

To a 200 ml. Parr pressure bomb equipped with a glass liner is charged 20 mls. of methanol, 0.30 gram (5.0 mmol) of glycolaldehyde and 0.05 gram of $RuH(O_2CCH_3)(P\phi_3)_3$, which is prepared as in Example 1. The contents of the bomb is stirred under gaseous nitrogen to dissolve the glycolaldehyde and the ruthenium carboxylate catalyst in the methanol solvent, and 400 psig of gaseous hydrogen is then charged to the reaction vessel. The vessel is then heated in an oil bath for 4 hours at 100° C., with continuous stirring of the liquid reaction mixture by means of a Teflon coated magnetic stirrer.

At the end of the above reaction time, a sample of the product mixture is taken and is analyzed by gas chromatography. Ethylene glycol is found to be produced in a yield of about 79% and a selectivity of about 79%, at a glycolaldehyde conversion of over 99%.

EXAMPLE 3

Following the procedure of Example 2, a liquid mixture containing 0.30 gram of glycolaldehyde, 0.002 gram of $RuH(O_2CCH_3)(P\phi_3)_3$ and 10 mls. of 2-propanol as solvent are contacted with 800 psig of gaseous hydrogen at 100° C. for three hours.

Analysis of the product mixture shows ethylene glycol to be produced in a yield of about 68% and a selectivity of about 68%, and shows glycolaldehyde conversion to be greater than 99%.

EXAMPLE 4

The procedure of Example 2 is repeated in separate runs employing 0.01 gram of the selected ruthenium catalyst, 20 mls. of methanol as solvent, 400 psig of hydrogen and a reaction temperature of 100° C. After 4 hours of reaction time, the selectivities to ethylene glycol and the acetaldehyde conversions are as set forth in Table I below. In each run no acetal by-product is detected.

TABLE I

| Run No. | Ru Complex | G. Ald.[1] % Conv. | EG[2] % Selectivity |
|---|---|---|---|
| 1 | $H(CH_3CO_2)Ru(P\phi_3)_3$ | 16 | 93 |
| 2 | $(CH_3CO_2)_2Ru(P\phi_3)_2$ | 49 | 94 |
| 3 | $H(\phi CO_2)Ru(P\phi_3)_3$ | 37 | 78 |

[1]G. Ald. = glycolaldehyde
[2]E.G. = ethylene glycol

EXAMPLE 5

The procedure of Example 4 is repeated except that the hydrogen pressure is increased to 800 to 1200 psig. After the 4 hours of hydrogenation at 100° C., the product mixtures are withdrawn and analyzed. The data thereby obtained as set forth in Table II below. In each run, no acetal by-product was detected.

TABLE II

| Run No. | Ru Complex [1] | $H_2$ (psig) | G. Ald.[2] % Conv. | EG[3] % Selectivity |
|---|---|---|---|---|
| 1 | $H(CH_3CO_2)Ru(P\phi_3)_3$ | 800 | 35 | 86 |
| 2 | $(CH_3CO_2)_2Ru(P\phi_3)_2$ | 1200 | 99 | 99 |
| 3 | $(CH_3CO_2)_2Ru(P\phi_3)_2$ | 800 | 66 | 85 |

[1]Sources of Ru complexes: Run 1 : Strem Chemical Company. Runs 2–3 : prepared as in Example 9.
[2]G. Ald. = glycolaldehyde
[3]E.G. = ethylene glycol

EXAMPLE 6 FOR COMPARISON

To illustrate the unexpectedly high activity and selectivity of the ruthenium carboxylates of this invention as homogeneous catalysts for the hydrogenation of glycolaldehyde to ethylene glycol, a series of runs are conducted following the procedure of Example 2 and using the indicated amounts of other ruthenium complexes which have been reported in the literature as catalysts for hydrogenation of a variety of other compounds. In each run, the liquid reaction mixture contains 0.30 gram of glycolaldehyde, 0.01 gram of the selected ruthenium complex and 20 mls. of the selected solvent. In each run, the liquid mixture is heated for 4 hours at 100° C. and the indicated pressures. The results thereby obtained are set forth in Table III.

TABLE III

| Run No. | Ru Complex [1] | Solvent | $H_2$ (psig) | G. Ald.[2] % Conv. | EG[3] % Selectivity | Acetal[4] % Selectivity |
|---|---|---|---|---|---|---|
| 1 | $RuCl_2(P\phi_3)_3$ | $CH_3OH$ | 400 | 99+ | 19 | 56 |
| 2 | $RuCl_2(P\phi_3)_3$ | $CH_3OH$ | 1200 | 99+ | 33 | 46 |
| 3 | $RuCl_2(P\phi_3)_3$ | $CH_3OH$ | 800 | 99+ | trace | 99 |
| 4 | $HRuCl(P\phi_3)_3$ | $CH_3OH$ | 800 | 99+ | trace | 99 |
| 5 | $RuCl_2(CO)_2(P\phi_3)_3$ | $CH_3OH$ | 800 | 99 | 10 | 88 |
| 6 | $RuCl_2(P\phi_3)_3$ | acetone | 800 | 99+ | 9 | —[5] |

[1]Sources of Ru complexes: Runs 1–3, 5 and 6: Strem Chemical Company. Run 4: Research Organic/Inorganic Chemical Corp. Note: As used in this application, "$\phi$" indicates a phenyl group.
[2]G. Ald. = glycolaldehyde.
[3]EG = ethylene glycol.
[4]Acetal = dimethyl acetyl of glycolaldehyde, $HOCH_2CH(OCH_3)_2$
[5]Selectivity to 2-hydroxymethyl-1,3-dioxolane = 13%

The above Runs illustrate the inactivity of ruthenium-carbonyl complexes for the hydrogenation of glycolaldehyde to ethylene glycol, and also show that chlororuthenium complexes are either not active catalysts for this reaction or effect very low selectivities to ethylene glycol, and form large amounts of acetal by-products.

EXAMPLE 7

The procedure of Example 2 is repeated employing 0.02 gram of $HRu(O_2CCH_3)(P\phi_3)_3$ catalyst and 0.30 gram glycolaldehyde and 20 ml. of methanol as solvent. A reaction temperature of 150° C., a $H_2$ pressure of 800 psig and a reaction time of 4 hours is employed.

Ethylene glycol is found to be produced at a yield of about 84% and a selectivity of about 84%, at a glycolaldehyde conversion of over 99%.

EXAMPLE 8

The procedure of Example 4 is repeated, except that 20 ml. of N,N-dimethyl acetamide is used as solvent, and the temperature and hydrogen pressure is increased to 150° C. and 1200 psig, respectively. At the end of the 4 hours of hydrogenation, the ethylene glycol yield is 81%, the ethylene glycol selectivity is 90%, and the glycolaldehyde conversion is 90%.

EXAMPLE 9

Preparation of $Ru(O_2CCH_3)_2(P\phi_3)_2$

Using the procedure of Example 1, 50 mls. of methanol, 5.0 gram of triphenylphosphine and 1.0 gram of ruthenium trichloride hydrate are stirred and heated to form tris(triphenylphosphine) ruthenium dichloride as a brown insoluble powder which is recovered by filtration. 1.0 Gram of this powder is dissolved in a mixture containing 50 mls. of tertiary butanol and 1.4 grams of sodium acetate trihydrate. The resulting mixture is heated with stirring at reflux temperature under $N_2$ for 4.5 hours to form an orange powder (0.44 gram) which is identified as the desired bis(acetato)bis(triphenylphosphine) ruthenium.

Hydrogenation of Glycolaldehyde

The procedure of Example 2 is repeated except that the catalyst is 0.02 gram of $Ru(O_2CCH_3)_2(P\phi_3)_2$, prepared as above, and the hydrogen pressure is 800 psig. After 4 hours of hydrogenation at 100° C., glycolaldehyde conversion is 99+% and the ethylene glycol yield is 98%, at a 98% ethylene glycol selectivity.

The preceeding run is repeated with another 0.02 gram sample of $Ru(O_2CCH_3)_2(P\phi_3)_2$ except that a temperature of 150° C. is used. After 4 hours, ethylene glycol yield and selectivity are each 94% and glycolaldehyde conversion is 99+%.

EXAMPLE 10 FOR COMPARISON

The procedure of Example 7 is repeated except the methanol in Example 7 is omitted and 20 ml. of water is employed. The ruthenium carboxylate catalyst, following stirring, is observed not to be dissolved in the aqueous medium. Employing a temperature of 120° C., a hydrogen pressure of 800 psig and a reaction time of 4.0 hours, no ethylene glycol is detected in the effluent withdrawn from the reaction vessel at the end of the 4 hours.

This illustrates the criticality of dissolving the selected ruthenium carboxylate catalyst of this invention in the liquid reaction medium, and also illustrates that water, of itself, is not a suitable solvent.

EXAMPLE 11

The procedure of Example 2 is repeated except that 5 ml. of water is employed and only 15 ml. of methanol is used. After stirring for dissolution of the glycolaldehyde and ruthenium carboxylate catalysts in the aqueous methanol solvent, the glycolaldehyde is hydrogenated at 400 psig hydrogen and a temperature of 150° C. for a period of 4 hours.

Ethylene glycol is found to be produced in a selectivity of about 65% and a yield of about 65%, at a glycolaldehyde conversion of over 99%.

EXAMPLE 12

The procedure of Example 2 is repeated except that the solvent comprises 25 ml. of acetone. At the end of 4 hours of reaction at 125° C. using a hydrogen pressure of 800 psig, ethylene glycol is found to be produced in a selectivity of about 62%, and a yield of about 62%, at a glycolaldehyde conversion of over 99%.

When the foregoing run is repeated at hydrogen pressure of 1200 psig, ethylene glycol selectivity and yields are each 84%, at a glycolaldehyde conversion over 99%.

The foregoing runs are repeated in a series of runs employing either 25 ml. of ethyl acetate or 25 ml. of benzonitrile as solvent, and substantially the same results are obtained.

EXAMPLE 13

The procedure of Example 2 is repeated in separate runs employing a temperature of 125° C. and a hydrogen pressure of 400 psig. After 4 hours of hydrogenation using 0.01 gram of $H(CH_3CO_2)Ru(P\phi_3)_3$ as catalyst, glycolaldehyde conversion is found to be 54%, ethylene glycol selectivity is 45% and a selectivity to the dimethyl acetal of glycolaldehyde is 20%.

In a separate run under the same conditions using 0.01 gram of $(CH_3CO_2)_2Ru(P\phi_3)_2$ is used as catalyst, glycolaldehyde conversion is 66% after 4 hours, and the selectivity to ethylene glycol and the dimethyl acetal is 75% and 4%, respectively.

The dimethyl acetal comprises about 0.4 wt. % and less than about 0.1 wt. % of the liquid reaction effluent in the first and second runs, respectively.

EXAMPLE 14 FOR COMPARISON

The procedure of Example 13 is repeated employing a reaction temperature of 100° C., and a reaction time of 16 hours. The ruthenium complex employed is $RuCl_2(P\phi_3)_3$. At the end of this 16 hours of reaction, the reaction effluent is found to contain ethylene glycol in a yield of about 65% and in a selectivity of about 65%, at a glycolaldehyde conversion of over 99%. Dimethyl acetal of glycolaldehyde is produced in a selectivity of 20% and comprises about 0.7 wt. % of the liquid reaction effluent. The foregoing procedure is repeated except that the hydrogenation pressure is increased to 1200 psig. After the 16 hours of reaction, glycolaldehyde conversion is found to be over 99%, and ethylene glycol selectivity and yield is found to be each about 55%. Dimethyl acetal is produced in this run in a selectivity of 45% and is present in the run's liquid reaction effluent in a concentration of about 1.5 wt. %.

When the foregoing results are compared with the ethylene glycol and acetal selectivities obtained in Example 13 using the ruthenium carboxylate catalysts of this invention, it can be seen that the above chlororuthenium couples, despite the 4-fold increase in reaction time, is a greatly inferior catalyst in the hydrogenation of glycolaldehyde to ethylene glycol.

EXAMPLE 15

Preparation of $H(CH_3CO_2)Ru(P\text{-}(p\text{-tolyl})_3)_3$

Using the procedure of Example 1, 50 mls. of methanol, 6.0 grams of tri-paratolylphosphine and 1.0 gram of ruthenium trichloride hydrate are stirred and heated at reflux under nitrogen for 24 hours to form tris(tri-paratolylphosphine) ruthenium dichloride as an insoluble powder which is recovered by filtration (4.2 grams). A portion of this powder (0.5 gram) is dissolved in a mixture containing 50 mls. of methanol and 0.5 gram of anhydrous sodium acetate. The resulting mixture is heated with stirring at reflux temperature under nitrogen for 5 hours to form yellow solids (0.21 gram) which are identified as the desired hydridoacetato ruthenium tris(tri-paratolylphosphine).

Hydrogenation of Glycolaldehyde

The procedure of Example 2 is repeated employing 0.02 gram of hydridoacetato tris(tri-paratolylphosphine) ruthenium as catalyst. After 4 hours of reaction at 125° C. and 800 psig, glycolaldehyde conversion is found to be 40% and ethylene glycol is found to be formed in a selectivity of about 64%. Selectivity to dimethylacetal of glycolaldehyde is 3%. The concentration of the acetal in the liquid reaction effluent is less than 0.1 wt. %.

EXAMPLE 16 FOR COMPARISON

Example 15 is repeated employing 0.02 gram of tris(triparatolylphosphine) ruthenium dichloride (prepared as in Example 14) in the hydrogenation of glycolaldehyde, except that the temperature during hydrogenation is increased to 150° C. After 4 hours of hydrogenation at 150° C. and 800 psig, glycolaldehyde conversion is found to be over 99%, and ethylene glycol is formed in a selectivity of about 70%. Dimethylacetal of glycolaldehyde is formed in a selectivity of 23%, and comprises 0.8 wt. % of the reaction effluent.

EXAMPLE 17

Preparation of H($\phi$CO$_2$)Ru(P$\phi_3$)$_3$

Following the procedure of Example 1, 1.0 gram of bis(triphenylphosphine) ruthenium dichloride, prepared as in Example 1, is dissolved in a mixture containing 150 mls. of methanol and 1.5 grams of sodium benzoate. The mixture is stirred and then heated under nitrogen by means of an oil bath and is maintained at reflux temperature for a period of 5 hours. This results in formation of a yellow precipitate, which is removed by filtration and is identified as the desired hydridobenzoato tris(triphenylphosphine) ruthenium (0.83 gram).

Hydrogenation of Glycolaldehyde

Following the procedure of Example 2, 0.05 gram of H($\phi$CO$_2$)Ru(P$\phi_3$)$_3$, prepared as above, 20 mls. of methanol and 0.30 gram of glycolaldehyde are charged to the reaction vessel. A gaseous hydrogen pressure of 800 psig is employed. Hydrogenation is effected for 4 hours at 125° C. At the end of this time, the product mixture is analyzed and ethylene glycol is found to be formed in a selectivity of 90% and a yield of 90%, at a glycolaldehyde conversion of greater than 99%. No dimethyl acetal of glycolaldehyde is detected in the product mixture.

EXAMPLE 18

The hydrogenation procedure of Example 15 is repeated except that 0.05 gram of hydridoacetato tris(triparatolylphosphine) ruthenium is employed as catalyst. After 4 hours of hydrogenation at 125° C. and 800 psig hydrogen, glycolaldehyde conversion is found to be over 99% and ethylene glycol selectivity is found to be 90%. Selectivity to dimethyl acetal of glycolaldehyde is only 2%, and the acetal concentration is less than 0.1 wt. % in the effluent.

EXAMPLE 19

The hydrogenation procedure of Example 2 is repeated except that the catalyst comprises 0.05 gram of bis(benzoato) bis(triphenylphosphine) ruthenium, and the reaction is conducted for 4 hours at a temperature of 125° C. and a hydrogen pressure of 800 psig. Glycolaldehyde conversion is found to be over 99%, and ethylene glycol is formed in a selectivity of 91% and in a yield of 91%.

EXAMPLE 20

The procedure of Example 2 is repeated in a series of runs using the selected amount of hydridoacetato tris(triphenylphosphine) ruthenium as catalyst. The hydrogenation is carried out at the selected temperature and hydrogen pressure for a period of 4 hours. The results thereby obtained are set forth in Table IV below.

TABLE IV

| Run No. | Catalyst (gm.) | Temp. (°C.) | H$_2$ (psig) | G. Ald.[1] % Conv. | E. G.[2] % Selec. | Acetal[3] % Selec. |
|---|---|---|---|---|---|---|
| 1 | 0.01 | 75 | 400 | 4 | 0 | 0 |
| 2 | 0.05 | 75 | 400 | 99+ | 88 | 0 |
| 3 | 0.01 | 125 | 400 | 54 | 45 | 20 |
| 4 | 0.05 | 125 | 400 | 99+ | 89 | 0 |
| 5 | 0.05 | 125 | 100 | 99+ | 71 | 0 |
| 6 | 0.01 | 75 | 1200 | 4 | 99 | 0 |
| 7 | 0.05 | 75 | 1200 | 99+ | 92 | 0 |

[1] Glycolaldehyde
[2] Ethylene Glycol
[3] Dimethylacetal of glycolaldehyde

Thus, whereas the rate of hydrogenation after 4 hours was too slow in run 1 to provide detectable ethylene glycol, the rates were much improved by increasing the amount of catalyst employed and/or temperature and the selectivities were markedly improved at increased hydrogen pressure.

From the foregoing Examples it can be seen that the ruthenium carboxylate catalysts of this invention achieve very low quantities of acetal by-products. Preferably, the process of this invention forms a product mixture, following hydrogenation, which is substantially free of acetal by-product, that is, the acetal by-product is present in the effluent in an amount of less than 0.1 wt. % of the effluent. As used herein the term "acetal by-product" is intended to refer to acetals formed during the hydrogenation from whatever source, and therefore includes acetals formed by reaction of glycolaldehyde with an alcohol solvent used in the hydrogenation, or by reaction of glycolaldehyde with the ethylene glycol product, or by reaction of two molecules of glycolaldehyde.

The source of the glycolaldehyde which is employed as feed in the practice of this invention is not in any way critical. It has been found that effluents from prior art hydroformylation processes, in which glycolaldehyde is formed from formaldehyde, can be used to provide the glycolaldehyde feed to the hydrogenation process of this invention. In particular, the effluents formed in European Patent Application No. 2,908 and German Pat. No. 2,741,589, which have been referred to above and which are hereby incorporated by reference, containing glycolaldehyde together with the hydroformylation catalyst of these processes and any unreacted formaldehyde, can be charged directly to the process of this invention wherein the said glycolaldehyde feed is contacted under the above-disclosed hydrogenation conditions with the ruthenium carboxylate catalyst of this invention for formation of ethylene glycol in excellent yields and selectivities. It has been surprisingly found that halide-containing hydroformylation catalysts, present in such glycolaldehyde feed to the process of this invention, do not adversely affect the performance of the instantly disclosed ruthenium carboxylate catalysts for hydrogenation of glycolaldehyde to ethylene glycol, and indeed do not result in the formation of significant acetal by-products. Whereas halide-containing ruthenium complexes result in formation of significant acetal by-products when used in hydrogenations of glycolaldehyde, it has been found that the ruthenium carboxylate catalysts of this invention are so active in the hydrogenation of glycolaldehyde that halide-containing hydroformylation catalysts, such as the rhodium chloride catalysts of the foregoing hydroformylation processes, do not significantly adversely affect the performance of the instantly disclosed ruthenium hydrogenation catalysts. Thus, the present invention offers the advantage of forming ethylene glycol from such hydroformylation effluents without the need to recover glycolaldehyde therefrom prior to hydrogenation and also without the need to remove any other constituents of the hydroformylation effluents prior to hydrogenation using a ruthenium carboxylate catalyst of this invention.

In such prior art hydroformylation processes, formaldehyde, carbon monoxide and hydrogen are reacted at elevated temperature and pressure in the presence of the selected hydroformylation catalyst to form glycolaldehyde. The hydroformylation step is generally performed at temperatures of from about 50° to 250° C., at $H_2$ pressures of from about 500 to 5,000 psig and at CO pressures of from about 500 to 5,000 psig. Typically, the gaseous carbon monoxide and hydrogen are employed in a $CO:H_2$ ratio of from about 1:10 to about 10:1 and preferably from about 1:5 to about 5:1. Formaldehyde is generally employed in an amount sufficient to provide a formaldehyde concentration of from about 1 to 25 wt. % in the reaction medium.

The hydroformylation catalyst employed in the hydroformylation step can comprise any of the rhodium catalysts disclosed in European Patent Application No. 2,908 and German Pat. No. 2,741,589. Thus, the hydroformylation catalyst can be elemental rhodium or a compound, complex or salt thereof, and mixtures thereof, which can be used as such or deposited or bound to a solid support, such as molecular sieve zeolites, aluminum oxide, silicon dioxide, anion exchange resin or a polymeric ligand. German Pat. No. 2,741,589 discloses the active form of the rhodium catalyst to be a complex combination or bond with carbon monoxide, e.g., rhodium carbonyl, which has additional ligands. These additional ligands include halides (e.g., chloride) and organic ligands, such as compounds containing at least one nitrogen atom and/or at least one oxygen atom such that the atoms contain a pair of electrons which are available to form coordination bonds with rhodium. Examples of organic ligands include various piperazines, dipyridyls, N-substituted diamines, aminopyridines, glycolic acid, alkoxy-substituted acetic acids, tetrahydrofuran, dioxane, 1,2-dimethoxybenzene, alkyl ethers or alkylene glycols, alkanolamines, aminodiacetic acid, nitrilotriacetic acid, ethylenediaminetetracetic acid, and ligands containing phosphorous such as trialkyl, triaryl and tricycloalkyl phosphites and triarylphosphines, as well as the analogous antimony and arsenic compounds. The rhodium hydroformylation catalyst can therefore be represented by the following formula (II):

$$RhX(CO)(PL_3)_2 \qquad (II)$$

wherein X is Cl, Br, I or F, and $PL_3$ is a phosphine ligand in which each L is an organo group, such as aromatic or alkyl groups, with aryl and alkyl aryl phosphine ligands being generally preferred.

The quantity of hydroformylation catalyst which is used, solvents (if any), the precise form of the catalyst (for example, whether the catalyst is supported or unsupported and is homogeneous or heterogeneous in the hydroformylation) and the like conditions are as disclosed in the foregoing European Patent Application No. 2,908 and German Pat. No. 2,741,589.

As indicated above, the effluent from the hydroformylation, containing glycolaldehyde, hydroformylation catalyst, and unreacted formaldehyde can be then charged as the glycolaldehyde feed to the hydrogenation process of this invention. The carbon monoxide gas employed in the hydroformylation should be removed prior to charging the effluent to the hydrogenation since it has been found that carbon monoxide gas can act as a poison for the ruthenium carboxylate catalysts of this invention. Thus, it is preferred that the hydrogenation be performed in the substantial absence of gaseous carbon monoxide, i.e., less than 0.1 psig CO.

The use of such hydroformylation effluents as feed for glycolaldehyde can be illustrated by the following Example.

EXAMPLE 21

To a 200 ml. Parr pressure bomb equipped with a glass liner is charged 25 mls. of N,N-dimethylacetamide, 0.05 gram of tris(tri-phenylphosphine) rhodium monochloride (marketed by Strem Chemical Company), and 1.0 gram of para-formaldehyde. The contents of the bomb is stirred under gaseous nitrogen to dissolve the rhodium catalyst and paraformaldehyde in the N,N-dimethylacetamide solvent, and the reaction vessel is then pressured with 600 psig carbon monoxide and 1200 psig gaseous hydrogen to provide a total pressure of 1800 psig above the liquid mixture. The vessel is then heated in an oil bath for 4 hours at 120° C., with continuous stirring of the liquid reaction mixture by means of a Teflon coated magnetic stirrer.

At the end of the above reaction time, a sample of the product mixture is taken and is analyzed by gas chromatography. Glycolaldehyde is found to be produced in an amount of 1.07 gram, which represents a glycolaldehyde yield of 54% based on the charged para-formaldehyde. Ethylene glycol is produced in a yield of only 1%, based on the para-formaldehyde charged.

The gases are vented from the reactor following the hydroformylation step to remove the gaseous carbon monoxide. The hydroformylation effluent is then transferred to a second 200 ml. Parr pressure bomb equipped with a glass liner and 0.05 gram of bis(triphenylphosphine) bis(acetato) ruthenium is charged as hydrogenation catalyst to the crude hydroformylation effluent. The contents of the second bomb are stirred under gaseous nitrogen to dissolve the ruthenium carboxylate hydrogenation catalyst in the N,N-dimethylacetamide solvent, and 1200 psig of gaseous hydrogen is then charged to the reaction vessel. Following the procedure of Example 2, the hydrogenation is conducted with stirring at a temperature of 150° C. for 4 hours. At the end of this time, glycolaldehyde conversion is found to be 88% and ethylene glycol is found to be produced in a selectivity of about 90%.

EXAMPLE 22

To further illustrate the ability of ruthenium carboxylate catalyst of this invention to efficiently hydrogenate glycolaldehyde even in the presence of prior art rhodium hydroformylation catalysts, the procedure of Example 2 is repeated employing as charge to the hydrogenation reactor 0.5 gram glycolaldehyde 0.05 gram tris(triphenylphosphine) rhodium monochloride, 0.05 gram tris(triphenylphosphine) hydrido acetato ruthenium as hydrogenation catalyst and 20 mls. of methanol. After stirring under gaseous nitrogen to dissolve the rhodium and ruthenium complexes in the methanol solvent, 1200 psig of gaseous hydrogen is charged. The hydrogenation reaction is conducted for 4 hours at 150°

C. At the end of this time, the hydrogenation reaction mixture is analyzed and ethylene glycol is found to be formed in a selectivity of 99%, at a glycolaldehyde conversion of over 99%, to provide a ethylene glycol yield of about 99%. No dimethyl acetal of glycolaldehyde was detected.

The ethylene glycol which is produced by the process of this invention can, as it has been indicated above, be recovered by known means from the effluent withdrawn from the hydrogenation reaction vessel. If desired, a carboxylic acid can be added to the hydrogenation effluent in order to convert the ethylene glycol to the corresponding carboxylic acid ester of ethylene glycol. Preferably, however, the ethylene glycol is recovered, again by known means, from the hydrogenation effluent and then, in a separate step is reacted with a carboxylic acid, to form the corresponding carboxylic acid ester of ethylene glycol. Suitable carboxylic acids include saturated aliphatic mono- and di-carboxylic acids having from 1 to 20 carbon atoms, such as acetic acid, propionic acid, isobutyric acid, n-butyric acid, and the like, and aromatic acids of up to 14 carbon atoms (e.g., benzoic and terephthalic acids).

The present invention, therefore, includes a two-step process for preparing carboxylic acid esters of ethylene glycol wherein, in a first step, glycolaldehyde is hydrogenated as above-described in the presence of a ruthenium carboxylate catalyst of this invention, the product ethylene glycol is recovered and, in a second step, the ethylene glycol is reacted with a carboxylic acid in liquid medium to form the corresponding carboxylic acid ester of ethylene glycol. The conditions of temperature and pressure under which the second-step ester-forming reaction is conducted are not critical and can vary widely. Generally, a temperature of from about 25° to 250° C. will be employed. An atmospheric, subatmospheric or superatmospheric pressure can be employed. The amount of carboxylic acid which is employed can also vary widely, although for a most complete reaction the carboxylic acid is preferably employed in an excess of that stoichiometrically required to react with the amount of ethylene glycol charged.

The presence of substantial amounts of strong acids, such as any of the strong mineral acids (e.g., hydrohalic acids, sulfuric, nitric, phosphoric and sulfonic acids) or any of the strong organic acids (e.g., trifluoroacetic acid) should be avoided in the process of this invention since it has been found that such acids cause the accelerated formation of unwanted by-products, e.g., unwanted acetal by-products. Accordingly, the liquid reaction medium of this invention is preferably substantially free of acids having an acid dissociation constant, $K_a$, of greater than $1 \times 10^{-2.5}$ at 25° C., i.e., acids having a $pK_a$ of less than 2.5. Preferably, the concentration of such acids should be less than 1 ppm.

Without intending to be limited by the following, it is believed that the ruthenium carboxylate catalysts which are charged to the process of this invention undergo a series of reactions with hydrogen and glycolaldehyde during the hydrogenation reaction to form ruthenium-carboxylate intermediate complexes in which at least one atom of hydrogen and/or glycolaldehyde is bonded to the carboxylate catalysts at a site vacated by one ligand. However, the precise form(s) of such ruthenium carboxylate intermediates is not known, and is not necessary for full understanding or use of this invention.

It will be obvious that various changes and modifications can be made without departing from the invention, and it is intended, therefore, that all matter contained in the foregoing description shall be interpreted as illustrative only and not as limitative of the invention.

I claim:

1. A process for the hydrogenation of glycolaldehyde to form ethylene glycol which comprises contacting glycolaldehyde with hydrogen in the presence of a liquid medium containing an organic solvent for the glycolaldehyde which may optionally contain water in which medium there is also dissolved a catalytic amount of at least one ruthenium carboxylate catalyst of the formula:

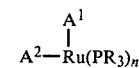

wherein n is 2 or 3, $A^1$ is hydrogen or a carboxylate moiety derived from an aliphatic saturated monocarboxylic acid of from 1 to 20 carbon atoms or from an aromatic monocarboxylic acid having from 7 to 14 carbon atoms, and substituted derivatives thereof, wherein the substituents comprise members selected from the group consisting of halo, alkyl of 1 to 10 carbon atoms, alkoxy of 1 to 8 carbon atoms, acyl of 1 to 10 carbon atoms, cyano, tertiary amido of from 2 to 14 carbon atoms, carboxyalkyl of from 2 to 10 carbon atoms, hydroxy and cycloalkyl of from 3 to 8 carbon atoms, $A^2$ is a carboxylate moiety derived from an aliphatic saturated monocarboxylic acid of from 1 to 20 carbon atoms or from an aromatic monocarboxylic acid having from 7 to 14 carbon atoms, and substituted derivatives thereof, wherein the substituents comprise members selected from the group consisting of halo, alkyl of 1 to 10 carbon atoms, alkoxy of 1 to 8 carbon atoms, acyl of 1 to 10 carbon atoms, cyano, tertiary amido of from 2 to 14 carbon atoms, carboxyalkyl of from 2 to 10 carbon atoms, hydroxy and cycloalkyl of from 3 to 8 carbon atoms, and R is phenyl or a mono- or poly-nuclear substituted or unsubstituted aryl of 7 to 14 carbon atoms wherein the substituents, if present, are halo, alkyl of 1 to 10 carbon atoms alkoxy of 1 to 8 carbon atoms, acyl of 1 to 10 carbon atoms, cyano, tertiary amido of from 2 to 14 carbon atoms, carboxyalkyl of from 2 to 10 carbon atoms, hydroxy and cycloalkyl of from 3 to 8 carbon atoms, with the proviso that n=3 when $A^1$ is hydrogen, to form said ethylene glycol.

2. The process according to claim 1 wherein said liquid medium is maintained at a temperature of from about 50° to 200° C.

3. The process according to claim 1 wherein $A^1$ is hydrogen and $A^2$ is alkanoate of from 1 to 4 carbon atoms.

4. The process according to claim 1 wherein $A^1$ and $A^2$ are each alkanoate of from 1 to 4 carbon atoms.

5. The process according to claim 1 wherein the organic solvent is selected from the group consisting of lower alkanols, aromatic solvents, glycols, aromatic and aliphatic nitriles, amides, ketones, esters and mixtures thereof.

6. The process according to claim 1 wherein the ruthenium carboxylate catalyst is employed in the liquid medium in an amount of from about 0.01 to about 20 weight %, based on the amount of glycolaldehyde charged to the process.

7. The process according to claim 3 wherein R is phenyl.

8. The process according to claim 4 wherein R is phenyl.

9. The process according to claim 1 wherein said ruthenium carboxylate catalyst is employed in said liquid reaction medium in an amount of at least $1 \times 10^{-5}$ mole of said catalyst, calculated as ruthenium, per mole of glycolaldehyde present in the liquid reaction medium.

10. The process according to claim 1 wherein the glycolaldehyde is obtained by hydroformylation of formaldehyde wherein formaldehyde is reacted with carbon monoxide and hydrogen in the presence of a hydroformylation catalyst.

11. The process according to claim 1 wherein $A^1$ and $A^2$ are the same.

12. The process according to claim 1 wherein $A^1$ is hydrogen.

* * * * *

UNITED STATES PATENT AND TRADEMARK OFFICE
CERTIFICATE OF CORRECTION

PATENT NO. : 4,317,946
DATED : March 2, 1982
INVENTOR(S) : Lawrence C. Costa

It is certified that error appears in the above–identified patent and that said Letters Patent are hereby corrected as shown below:

Col. 3, line 17 - delete "i" after 87
Col. 9, line 53 - the second "to" should be --or--

Signed and Sealed this

Twenty-first Day of June 1983

[SEAL]

Attest:

DONALD J. QUIGG

Attesting Officer    Acting Commissioner of Patents and Trademarks